(12) United States Patent
Yaralioglu et al.

(10) Patent No.: US 6,789,426 B2
(45) Date of Patent: Sep. 14, 2004

(54) MICROFLUIDIC CHANNELS WITH INTEGRATED ULTRASONIC TRANSDUCERS FOR TEMPERATURE MEASUREMENT AND METHOD

(75) Inventors: Goksen G. Yaralioglu, Palo Alto, CA (US); Arif S. Ergun, Mountain View, CA (US); Hemanth Jagannathan, Palo Alto, CA (US); Butrus T. Khuri-Yakub, Palo Alto, CA (US)

(73) Assignee: Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 10/198,290

(22) Filed: Jul. 17, 2002

(65) Prior Publication Data

US 2003/0029242 A1 Feb. 13, 2003

Related U.S. Application Data

(60) Provisional application No. 60/309,245, filed on Jul. 31, 2001.

(51) Int. Cl.[7] .......................... G01H 5/00; G01K 11/24
(52) U.S. Cl. ........................................ 73/597; 374/119
(58) Field of Search .................. 73/597, 622; 374/119, 374/117

(56) References Cited

U.S. PATENT DOCUMENTS

| | | | |
|---|---|---|---|
| 4,655,992 A | * | 4/1987 | McKnight et al. .......... 374/119 |
| 5,360,268 A | | 11/1994 | Hayashi et al. |
| 5,619,476 A | | 4/1997 | Haller et al. |
| 5,870,351 A | | 2/1999 | Ladabaum et al. |
| 5,894,452 A | | 4/1999 | Ladabaum et al. |
| 6,026,688 A | | 2/2000 | Khuri-Yakub et al. |
| 6,151,558 A | | 11/2000 | Conant et al. |
| 6,250,161 B1 | | 6/2001 | Khuri-Yakub et al. |

OTHER PUBLICATIONS

H. Jagannathan et al., "Micro–Fluidic Channels with Integrated Ultrasonic Transducers," 2001 IEEE Ultrasonic Symposium, Oct. 7–10, 2001, pp. 859–862.*

* cited by examiner

*Primary Examiner*—John E. Chapman
(74) *Attorney, Agent, or Firm*—Dorsey & Whitney LLP

(57) ABSTRACT

There is described a method and apparatus for measuring temperature of a fluid in a microchannel of the type having spaced walls. An ultrasonic transducer transmits ultrasonic waves transmitted from one wall to the opposite wall. A processor determines the time-of-flight of the ultrasonic waves from the one wall and reflected to the opposite wall to the one wall. The processor converts the time-of-flight to velocity by dividing the distance between walls by the time-of-flight. The processor converts velocity to temperature from the relationship of velocity to temperature in the fluid.

4 Claims, 4 Drawing Sheets

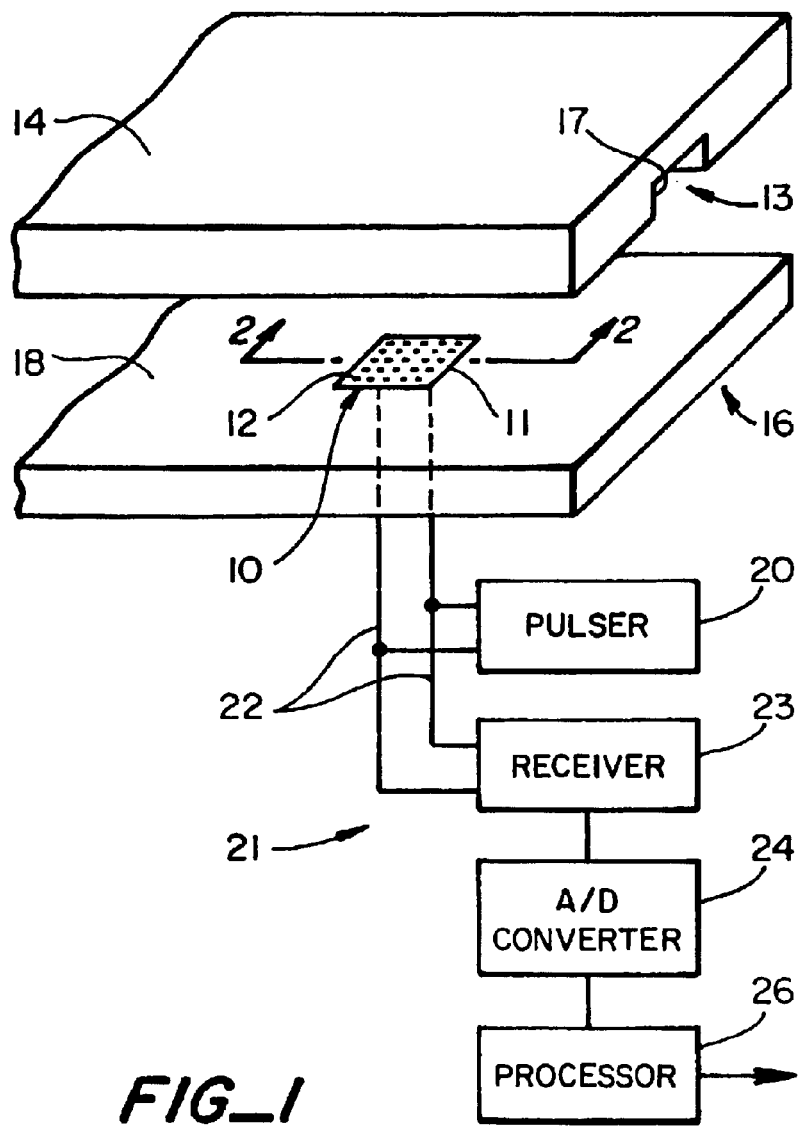
FIG_1
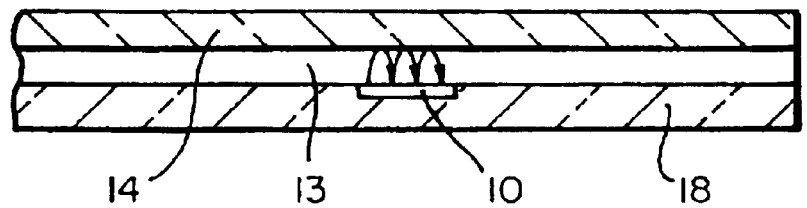
FIG_2

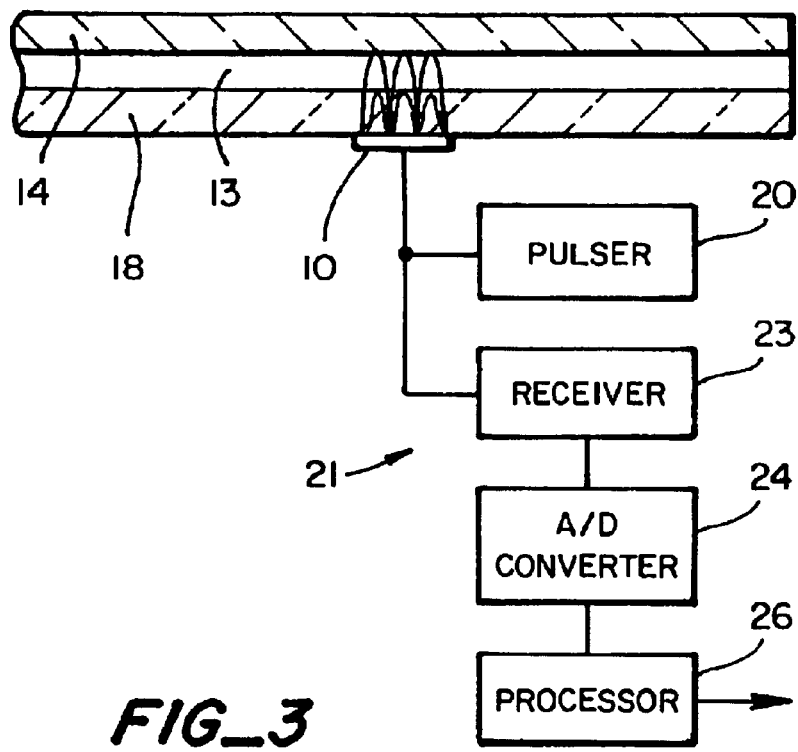
FIG_3
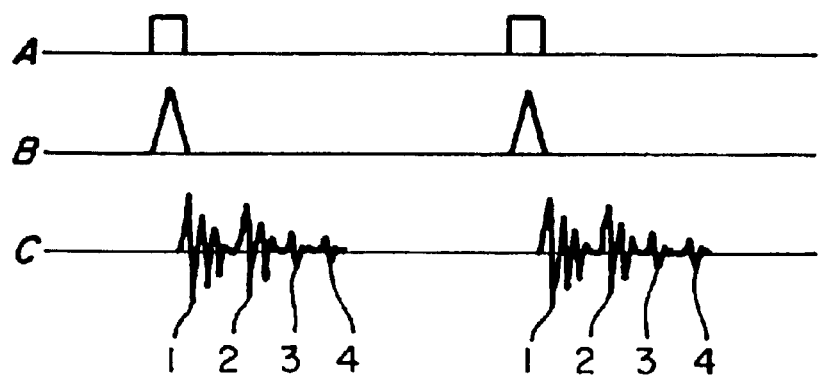
FIG_4

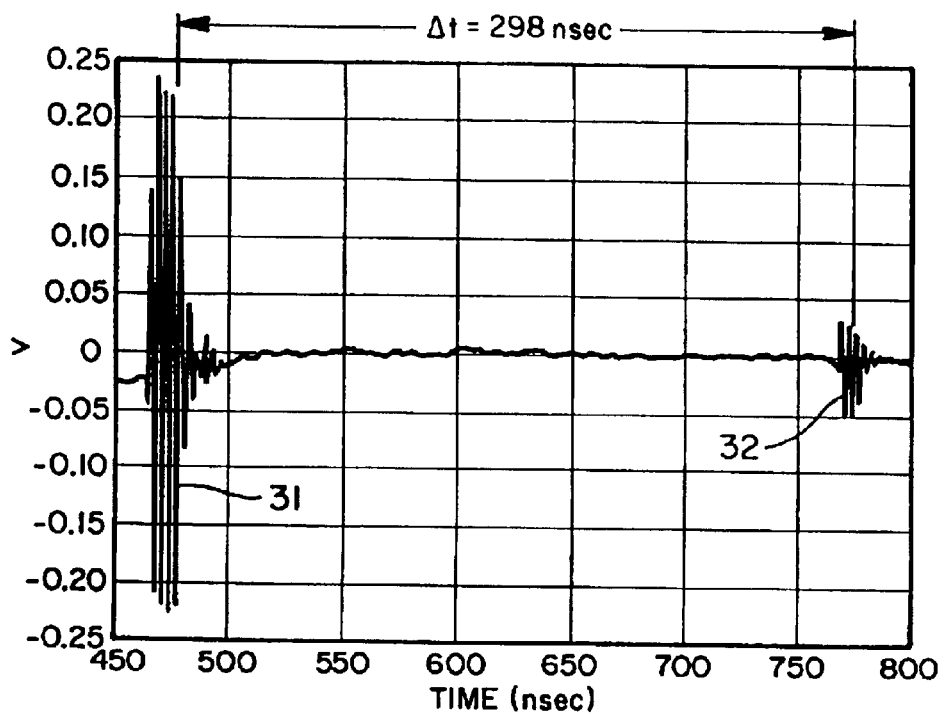
FIG_5
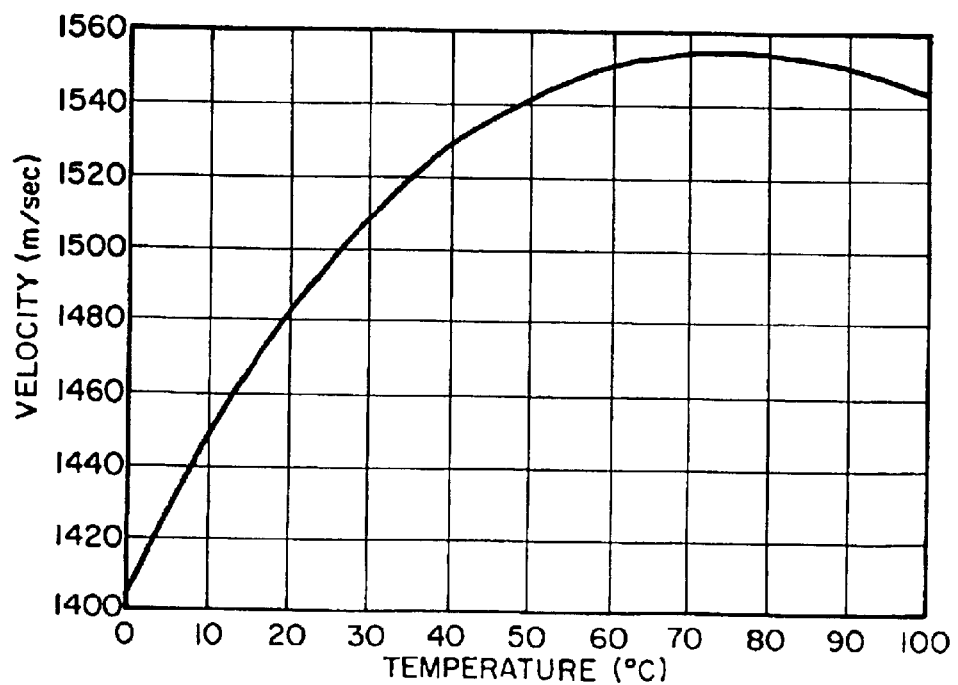
FIG_6

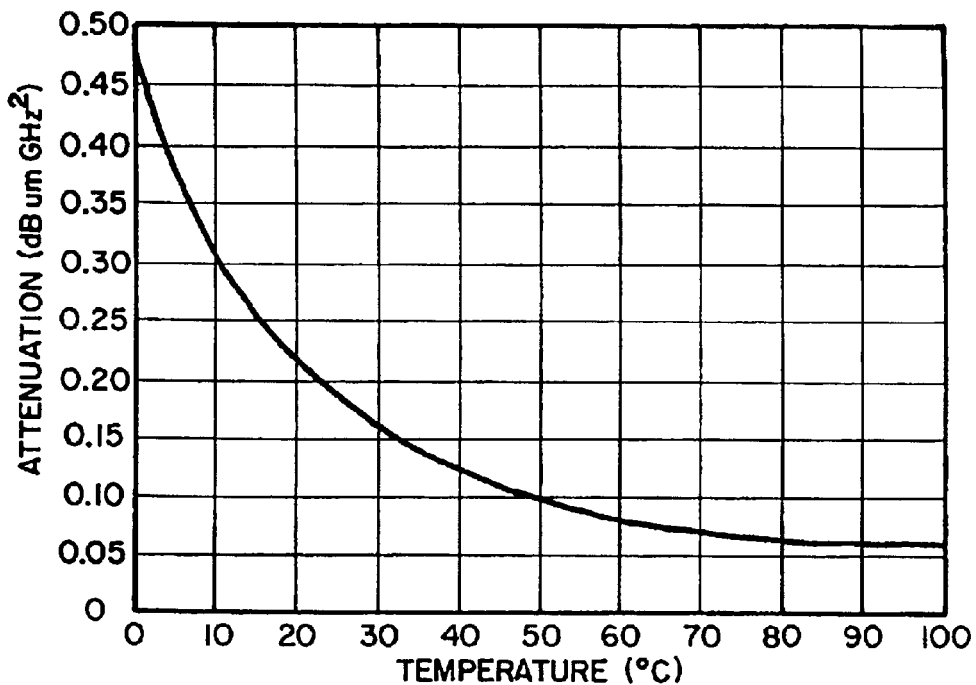
FIG_7
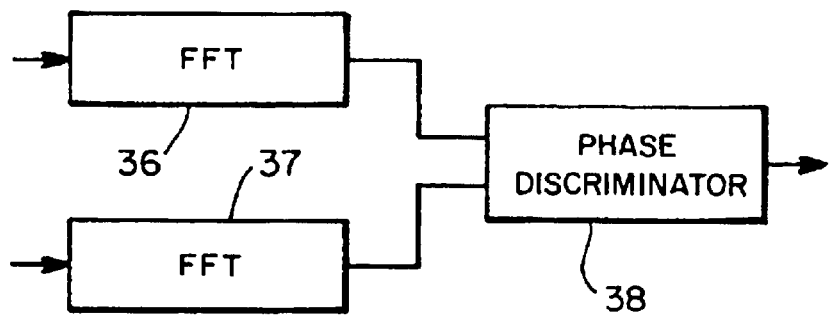
FIG_8

MICROFLUIDIC CHANNELS WITH INTEGRATED ULTRASONIC TRANSDUCERS FOR TEMPERATURE MEASUREMENT AND METHOD

RELATED APPLICATIONS

This application claims priority to Provisional Application Ser. No. 60/309,245 filed Jul. 31, 2001.

GOVERNMENT SUPPORT

This invention was made with Government support under Contract No. N 66001-00-C-8077 awarded by the Navy. The Government has certain rights in this invention.

BRIEF DESCRIPTIONS OF THE INVENTION

This invention relates generally to microfluidic devices having microfluidic channels with integrated ultrasonic transducers for measuring the temperature of fluids in said channels and more particularly to such devices employing ultrasonic transducers such as integrated micromachined ultrasonic transducers (MUTs) or piezoelectric transducers.

BACKGROUND OF THE INVENTION

The large investments in the microelectronics industry converted integrated circuits laboratories into machine shops where miniature electromechanical systems are designed and built. Electromechanical as well as electro-optical systems have been miniaturized and used in many different applications. In the same fashion, miniaturization is presently applied in the field of microfluidics. Microfluidics technology provides the advantage of being able to perform chemical and biochemical reactions and/or separations with high throughput low volumes. Microfluidic systems employ microchannels formed in substrates or chips in which chemical and biochemical materials are transported, mixed, separated and tested.

One of the parameters measured such microfluidic systems is the temperature of the fluids and the change in temperature of fluids as a result of any reactions carried out in the channel.

A typical method for temperature measurement involves using a thermocouple embedded in the substrate, preferably close to the fluidic channel. However, this method measures the average temperature of the substrate and fluid. In most cases, the channel is so small that the thermocouple reading is dictated primarily by the substrate temperature.

There is a need for directly measuring the temperature of fluids in microchannels.

OBJECTS AND SUMMARY OF THE INVENTION

It is an object of the present invention to provide a system and method for measuring the temperature of fluids in a channel using ultrasonic transducers.

It is another object of the present invention to provide a system for measuring the temperature of fluids in a channel using integrated ultrasonic transducers such as micromachined capacitive or piezoelectric transducers.

Micromachining permits fabrication of ultrasonic transducers having sizes compatible with the microchannels of microfluidic devices. Furthermore, the transducers can be integrated into the microchannels. Capacitive micromachined ultrasonic transducers (cMUTs) operating both in air and water are known and described in U.S. Pat. Nos. 5,619,476; 5,870,351 and 5,894,452. In both air and water, a Mason electrical equivalent circuit is used to represent the transducers and predict their behavior (W. P. Mason, *Electromechanical Transducers and Wave Filters* (Van Nostrand, N.Y., 1942)). These transducers are fabricated using standard IC processes and have been integrated with signal processing electronics to form an integrated system. In the article entitled "Highly Integrated 2-D Capacitive Micromachined Ultrasonic Transducers" appearing in IEEE Ultrasonic Symposium Proceedings pp. 1163–1666, 1999, S. Calmes et al., describe the fabrication of cMUTs with through wafer connections so that they can be flip-chip bonded to chips having signal processing electronics. Alternatively, the processing electronics can be implemented on the same silicon wafer avoiding the through wafer via structure. The dynamic range and bandwidth of cMUTs surpass their piezoelectric counterparts while being completely compatible with microfluidic chip fabrication processes.

Capacitive micromachined ultrasonic transducers (cMUTs) with dimensions of 100 $\mu$m or less are fabricated on the walls of the fluidic channels and operate in the 1–100 MHz frequency range. The cMUTs are surface micromachined to have a low surface profile, permitting undisturbed fluid flow. These transducers enable in-situ measurements of temperature of the fluid in the channel by measuring the velocity and/or attenuation of sound waves in the fluid in the channel.

Ultrasonic transducers having the above-described characteristics can also be micromachined from piezoelectric material. They may be formed by thin film deposition such as sputtering, sol-gel deposition or other types of physical or chemical deposition. Through wafer interconnects can be used with piezoelectric transducers.

The present invention provides a temperature measuring system in which ultrasonic transducers fabricated in one wall of the channel or placed on the substrate opposite the channel generate ultrasonic waves which reflect from one or both walls of the channel and provide an output signal representative of the velocity of the sound waves or attenuation or both in the fluid. The signals are then processed to provide the fluid temperature.

BRIEF DESCRIPTION OF THE DRAWINGS

FIG. 1 is a perspective view of a portion of a microfluidic channel including an ultrasonic transducer and signal processing electronics connected to the transducer by through wafer connections.

FIG. 2 is a sectional view of the microfluidic device of FIG. 1 including a top cover to form a channel and taken generally along the line 2—2 of FIG. 1.

FIG. 3 is a sectional view of a microfluidic channel with the cMUT mounted on the bottom of the device substrate and including signal processing electronics connected to the ultrasonic transducer.

FIGS. 4A–4C show the generation of ultra sonic pulses applied to the transducers of FIG. 1 or 3 and the reflected waves from the interfaces or walls of the microfluidic channel.

FIG. 5 is a typical oscilloscope trace showing a first pulse as applied to the transducer or as reflected on the bottom of the microfluidic channel in FIG. 3 and the pulse reflected from the top wall of the microfluidic channel.

FIG. 6 shows acoustical velocity in distilled water as a function of temperature.

FIG. 7 shows attenuation in distilled water as a function of temperature.

FIG. 8 schematically shows a processing circuit for measuring phase differences between reflected pulses.

DESCRIPTION OF PREFERRED EMBODIMENTS

The ultrasonic transducer 10 shown in FIG. 1 comprises a cMUT 11 which includes a plurality of cells 12. Each cell is made of vacuum-sealed fully supported membrane with a diameter of 5–200 micrometers. For example a 100 micrometer square transducer with individual cells 20 micrometers in diameter could be made with 25 small membranes. A detailed description of the method of fabrication and operation of cMUTs is found in U.S. Pat. Nos. 5,619,476; 5,870,351 and 5,894,452 incorporated herein in their entirety by reference.

In microfluidic technology, the chemical or biochemical reactions and/or separations take place in microchannels having dimensions in the range of 1 micron to 500 microns or more. Ultrasonic waves are ideal for measuring the temperature of fluids in the channel. In accordance with one embodiment of the present invention, a cMUT 11 is integrated into the walls of the microchannel, FIGS. 1 and 2, or affixed to the wall of the microfluidic device substrate, FIG. 3. In another embodiment of the present invention, the ultrasonic transducer 10 comprises a micromachined piezoelectric transducer fabricated as described above.

Referring to FIGS. 1 and 2, a microchannel 13 is shown in the top 14 of a microfluidic device 16. The microchannel can, for example, have dimensions 1 micron to 500 microns or more depending upon the application of the device. The channels can be formed by micromachining a groove 17 in the top plate 14 and suitably sealing the top plate to the bottom substrate 18. The top plate 14 can be glass, silicon or the like in which the groove is machined, or it can be a polymetric material which can be machined or molded with the groove 17. In accordance with one embodiment of the present invention the bottom substrate 18 is a semiconductor material such as silicon which is processed as described above to form the integrated cMUT 11. The top surface of the CMUT is substantially co-extensive with the bottom wall of the channel 13. This minimizes the influence of the CMUT on the fluid flow. The cMUT can be connected to known excitation and detector electronics 21 using through device leads 22 and flip-chip bonding techniques to bond the integrated detector electronics 21. Such techniques are described in Oralkan (O. Oralkan, XC. Gin, F. L. Degertekin and B. T. Khuri-Yakub, "Simulation and experimental characterization of a #2-D CMUT array element, IEEE TRANS. UFFC, 46, pages 1337–40, 1999).

Alternatively cMUT may be formed in or attached to the bottom of the substrate 18 as shown in FIG. 3. In still another embodiment, the ultrasonic transducer is a piezoelectric material which is deposited in the channel or on the bottom of the substrate. The substrate can be any material such as glass, plastic, etc., since the transducer is formed by deposition.

In accordance with the present invention the ultrasonic transducer 10 is used to measure velocity and/or attenuation of sound waves traveling through the liquid flowing along the microchannel. The sound velocity or attenuation can be converted to temperature by using a calibration curve, which relates the liquid temperature to the acoustic properties of the liquid. This technique can be used to determine the temperature of the fluid in the channel and temperature of chemical reactions occurring inside the microfluidic channels.

The acoustic properties of liquid change dramatically with temperature. FIGS. 6 and 7 show the value of sound velocity and attenuation respectively at different temperatures for pure water.

FIGS. 1 and 3 show a pulser 20 which generates pulses such as the pulses 21, FIG. 4A, which are applied to the cMUT, FIG. 4B, which causes the cMUT to resonate and generate the acoustic waves designated by the numeral 1, FIG. 4C. The operating frequency is determined by the size of the cells and the spacing of the membrane from the substrate in each of the cells. The transducer causes mechanical displacement which launches the acoustic waves, FIG. 4C. When a piezoelectric ultrasonic transducer is employed, the generation of acoustic waves is well known. In FIG. 1 the waves are launched directly through the fluid flowing in the channel whereas in FIG. 3 the waves are launched through the substrate and through the channel 13. Referring to FIG. 2, the acoustic waves reflect from the upper wall of the channel and are received by the transducer as shown by the numeral 2, FIG. 4C. The input signal 1 and reflected signal 2 are received by a receiver 23. The signals are applied to an analog digital converter 24 and then to a processor 26. Referring to FIG. 4C, additional reflections from various other surfaces are shown as pulses 3 and 4. Referring to FIG. 5 a typical input wave obtained by an oscilloscope is shown at 31 while the first reflective wave is shown at 32. In this illustration a time lapse for travel of the sonic wave to the upper wall and return is 298 nanoseconds. The processor may count the lapsed time between the emitted and reflected wave, or if the waves are quite close, a processing circuit such as that shown in FIG. 8 may be incorporated in the processor. The processing circuit, FIG. 8, includes fast Fourier transforms 36 and 37 and phase discriminator 38 which provides the phase difference between the launched wave 31 and return wave 32. This is then converted to elapsed time. The elapsed time can be converted to velocity by the following equation:

$$v = \frac{2h}{\Delta t}$$

where h is the channel height and $\Delta t$ is the time separation or lapse between two pulses. For example, if the channel height is 223 microns using the delay of 298 nanoseconds with pure water inside the channel and using the relationship shown in FIG. 6, the fluid temperature is calculated to be 25° C. As explained above if the two pulses are not well separated it is possible to measure the delay using the spectrum of two or more pulses having minimas separated by $\Delta t$. The separation of these minimum points is given by $\Delta f = 1/\Delta t$ provided that the pulses have the same amplitude and phase. The time-of-flight, and consequently the sound velocity within the channel, can be determined by measuring the frequency separation. Sound velocity can then be used to measure or monitor the fluid temperature. More accurate evaluations may involve a simulation program which calculates the phase and amplitude of acoustic pulses after propagating through the glass and liquid.

The present method is substantially immune to substrate temperature fluctuations since the relative delay between pulses reflecting from the bottom and top of the channel is measured. Thus, there has been provided a novel method and apparatus for measuring temperature of fluids in microfluidic channels.

What is claimed is:

1. A sensor for sensing velocity of ultrasonic waves in fluids in microchannels formed in a microfluidic device comprising:

a capacitive micromachined ultrasonic transducer integrated in one wall of the channel, a pulser for applying electrical pulses to said ultrasonic transducer to transmit ultrasonic waves which travel through the fluid in said channel and reflect from the opposite wall of said channel, said transducer adapted to receive ultrasonic waves reflected from the opposite wall and generate an output signal, an analog to digital converter connected to received said output signals and provide a representative digital output, and a processor configured to receive said digital output and determine the time of travel of ultrasonic waves through the fluid and to determine from the time of travel and the distance the ultrasonic waves travel through the fluid the velocity of the ultrasonic waves in the fluid.

2. A sensor as in claim 1 in which the processor includes a look-up table showing the velocity of the fluid as a function of temperature whereby the processor compares the velocity of the ultrasonic waves in the fluid to the look-up table to provide an output representative of temperature.

3. A sensor for sensing velocity of sound in fluids in microchannels formed in a microfluidic device comprising:

a capacitive micromachined ultrasonic transducer integrated into one wall of said microchannel;

a pulser for applying electrical pulses to said ultrasonic transducer to transmit ultrasonic waves which travel through the fluid in said channel and reflect from the opposite wall of said channel, said transducer adapted to receive ultrasonic waves and generate an output signal; and a processor circuit configured to receive the electrical pulses and the output signal and determine the velocity of the ultrasonic waves by measuring the phase difference between the transmitted ultrasonic waves and the received ultrasonic waves.

4. A sensor as in claim 3 in which the processor includes a look-up table showing the velocity of the fluid as a function of temperature whereby the processor compares the velocity of the ultrasonic waves in the fluid to that in the look-up table to provide an output representative of temperature.

* * * * *